(12) United States Patent
Rogers

(10) Patent No.: US 11,839,863 B2
(45) Date of Patent: Dec. 12, 2023

(54) METHOD, APPARATUS, AND COMPUTER-READABLE MEDIA FOR VORTEX ARC REACTOR

(71) Applicant: Michael W. Rogers, El Dorado, AR (US)

(72) Inventor: Michael W. Rogers, El Dorado, AR (US)

( * ) Notice: Subject to any disclaimer, the term of this patent is extended or adjusted under 35 U.S.C. 154(b) by 86 days.

(21) Appl. No.: 16/902,416

(22) Filed: Jun. 16, 2020

(65) Prior Publication Data

US 2020/0306718 A1    Oct. 1, 2020

Related U.S. Application Data

(62) Division of application No. 15/791,702, filed on Oct. 24, 2017, now abandoned.

(Continued)

(51) Int. Cl.
*B01J 19/24*  (2006.01)
*B01J 19/08*  (2006.01)
(Continued)

(52) U.S. Cl.
CPC .............. *B01J 19/2405* (2013.01); *B01J 8/14* (2013.01); *B01J 19/088* (2013.01);
(Continued)

(58) Field of Classification Search
CPC ........ B01J 19/2405; B01J 8/14; B01J 19/088; B01J 19/1806; B01J 19/26;
(Continued)

(56) References Cited

U.S. PATENT DOCUMENTS 3,395,194 A    7/1968    Keckler
5,427,747 A    6/1995    Kong
(Continued)

OTHER PUBLICATIONS

Transmittal; International Search Report ;and the Written Opinion of the International searching Authority for International Application No. PCT/US2017/057998.
(Continued)

*Primary Examiner* — Xiuyu Tai
(74) *Attorney, Agent, or Firm* — Katten Muchin Rosenman LLP

(57) ABSTRACT

Vortex arc reactor apparatus and method provide a nozzle with converging, throat, and diverging portions. Input structure inputs a reactant and an oxidant into the converging portion. Ignition structure ignites the input reactant and oxidant. A vortex-creating structure creates a vortex of the ignited reactant and oxidant in the converging portion. The input structure, the vortex-creating structure, and the nozzle converging and throat portions are configured to provide a throat-portion-vortex of ignited reactant and oxidant that has an angular velocity which provides (i) negatively-charged particles in an exterior portion of the throat-portion-vortex, (ii) positively-charged particles in an interior portion of the throat-portion-vortex, and (iii) at least one arcing reaction between the positively-charged particles and the negatively-charged particles, to form syngas and at least one aromatic liquid in the nozzle diverging portion. Gas/liquid separation structure is preferably configured to separate the formed syngas from the at least one aromatic liquid.

10 Claims, 8 Drawing Sheets

Related U.S. Application Data

(60) Provisional application No. 62/411,761, filed on Oct. 24, 2016.

(51) Int. Cl.

| | |
|---|---|
| *C01B 3/36* | (2006.01) |
| *C01B 3/32* | (2006.01) |
| *C10G 50/00* | (2006.01) |
| *C07C 2/80* | (2006.01) |
| *C07C 2/82* | (2006.01) |
| *B01J 19/26* | (2006.01) |
| *B01J 8/14* | (2006.01) |
| *B01J 19/18* | (2006.01) |

(52) U.S. Cl.
 CPC ......... *B01J 19/1806* (2013.01); *B01J 19/26* (2013.01); *C01B 3/32* (2013.01); *C01B 3/36* (2013.01); *C07C 2/80* (2013.01); *C07C 2/82* (2013.01); *C10G 50/00* (2013.01); *B01J 2208/00867* (2013.01); *B01J 2219/00119* (2013.01); *B01J 2219/0805* (2013.01); *B01J 2219/0875* (2013.01); *C01B 2203/0255* (2013.01); *C01B 2203/1223* (2013.01); *C01B 2203/1241* (2013.01); *C10G 2300/1025* (2013.01); *C10G 2400/30* (2013.01)

(58) Field of Classification Search
 CPC .... B01J 2208/00867; B01J 2219/00119; B01J 2219/0805; B01J 2219/0875; B01J 2219/00159; B01J 2219/00123; B01J 2219/00157; B01J 2219/00155; B01J 2219/00094; B01J 2219/00164; B01J 2219/00058; C01B 3/32; C01B 3/36; C01B 2203/0255; C01B 2203/1223; C01B 2203/1241; C01B 3/384; C01B 3/363; C01B 2203/0816; C01B 2203/141; C01B 2203/142; C01B 2203/0233; C07C 2/80; C07C 2/82; C10G 50/00; C10G 2300/1025; C10G 2400/30; C10G 1/00; C10B 49/04; C10B 53/00; C10B 3/02; C10J 3/54; C10J 3/56; C10J 2300/0956; C10J 2300/1238; C10J 2300/0943; C10J 2200/09; C10J 2300/093; C10J 2300/0973; C10J 2300/123; C10J 2300/0959; C10J 2300/0969; C10J 2300/0983; C10J 2300/0946; C21B 5/001; C21B 13/0073; C21B 13/02; C21B 2100/64; C21B 2100/22; C22B 5/12; C22B 4/005; C21C 5/56; C21C 5/5217; Y02P 10/134; Y02P 20/141; Y02P 10/20; Y02P 10/143; B01F 25/31232; B01F 25/3121; B01F 25/312532; B01F 23/10; H01M 8/04201; H01M 8/0606; H01M 8/0612; C02F 3/02; F23C 6/047; C04B 18/04; C04B 7/4453; B23K 10/00; D21C 11/12; H01J 37/32009; C01F 11/18; C01F 11/46; C01F 11/24; H05H 1/44; H05H 1/42; Y10S 588/90

See application file for complete search history.

(56) References Cited

U.S. PATENT DOCUMENTS

| | | |
|---|---|---|
| 5,749,937 A | 5/1998 | Detering |
| 5,935,293 A | 8/1999 | Detering |
| 5,997,596 A | 12/1999 | Joshi |
| 6,187,226 B1 | 2/2001 | Detering |
| 6,372,019 B1 | 4/2002 | Alferov et al. |
| RE37,853 E | 9/2002 | Detering |
| 6,513,345 B1 | 2/2003 | Betting et al. |
| 7,008,970 B2 | 3/2006 | Kong |
| 7,097,675 B2 | 8/2006 | Detering |
| 9,005,536 B1* | 4/2015 | Rogers .................. C05C 11/00 422/186.21 |
| 2004/0208805 A1 | 10/2004 | Fincke |
| 2008/0277265 A1* | 11/2008 | Tsangaris ............... C01B 3/386 204/422 |
| 2012/0022287 A1 | 1/2012 | Subramaniam et al. |
| 2012/0180668 A1 | 7/2012 | Borissov et al. |
| 2015/0024297 A1 | 1/2015 | Finnerty et al. |
| 2015/0315475 A1 | 11/2015 | Rogers |
| 2016/0194202 A1 | 7/2016 | Rabinovich et al. |

OTHER PUBLICATIONS

D. Wright et al., "Modeling of electric arcs: A study of the non-convective case with strong coupling", J. Plasma Physics, pp. 1-15, Feb. 18, 2013.

Yi Chang and E. Pfender, "Thermochemistry of Thermal Plasma Chemical Reactions. Part I. General Rules for the Prediction of Products", Plasma Chemistry and Plasma Processing, vol. 7, No. 3, pp. 275-276, Apr. 10, 1987.

Queno et al., "Mechanism of Ion Formation in High-Temperature Flames", Symposium (International) on Combustion, vol. 8, Issue 1, 1961, p. 222.

Georgio De Vera, "The Ranque-Hilsch Vortex Tube" May 10, 2010.

J. Wu, et al., "Shear layer vortices and longitudinal vortices in the near wake of circular cylinder", Experimental Thermal and Fluid Science 12(2): 169-174 Feb. 1996, 6 sheets.

S M Reshetnikov, et al., "The distribution of excess charges in the diffusion flame of hydrocarbons", 2016 Journal of Physics: Conference Series, 669 012040, doi:10.1088/1742-6596/669/1/012040, 5 sheets.

"Edmund Davy Inventor of Acetylene, Biography of Edmund Davy", Researchpedia, Academic Heaven, Sep. 6, 2014, https://researchpedia.info/edmund-davy-inventor-of-acetylene/, 4 sheets.

"The 100 Most Important Chemical Compounds", 3. Acetylene, pp. 7-9, 3 sheets.

"Acetylene: cornerstone of a firm foundation", pp. 1-5, https://www.basf.com/cn/en/media/BASF-Information/Innovation/Acetylene-cornerstone- . . . , 5 sheets.

Peter C. Kong et al., "Plasma Processing of Hydrocarbon", Idaho National Laboratory, Electric Power 2007, May 2007, 12 sheets.

Timothy Wayne Pederson, "Ionic structures of methane flames", Iowa State University 1991, p. 17, 103 sheets.

P. Delmont & M. Torrilhon, "Modeling and strongly coupled simulation of electric arc extinction in an electrical network", 40th EPS Conference on Plasma Physics, MathCCES, RWTH Aachen University, Germany, p. 5.412, 1 sheet.

Rudolf Hilsch, "The Use of the Expansion of Gases in a Centrifugal Field as Cooling Process", The Review of Scientific Instruments, vol. 18 (2), pp. 108-113, (1947), translation of an article in time, Natural science, 1 (1946) p. 208.

Non-Final Rejection dated Sep. 5, 2019, from U.S. Appl. No. 15/791,702, 23 sheets.

* cited by examiner

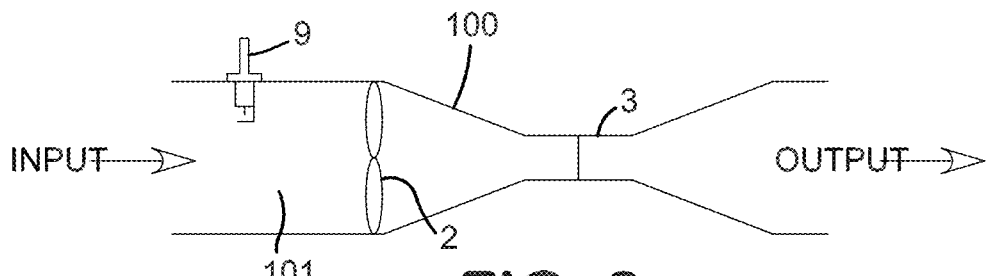
FIG. 2a
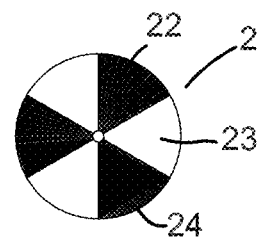
FIG. 2b1
FIG. 2b2
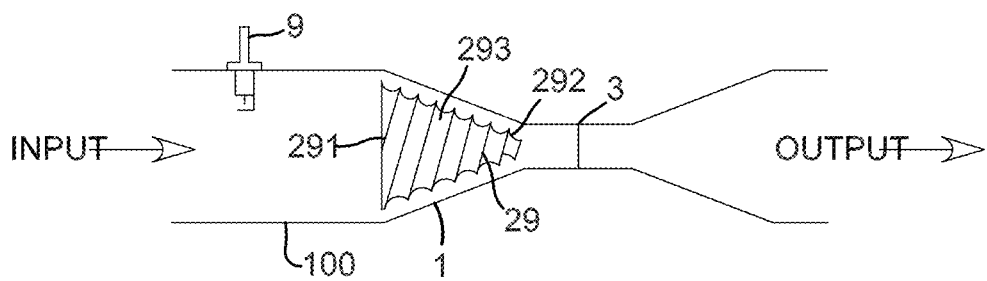
FIG. 2c

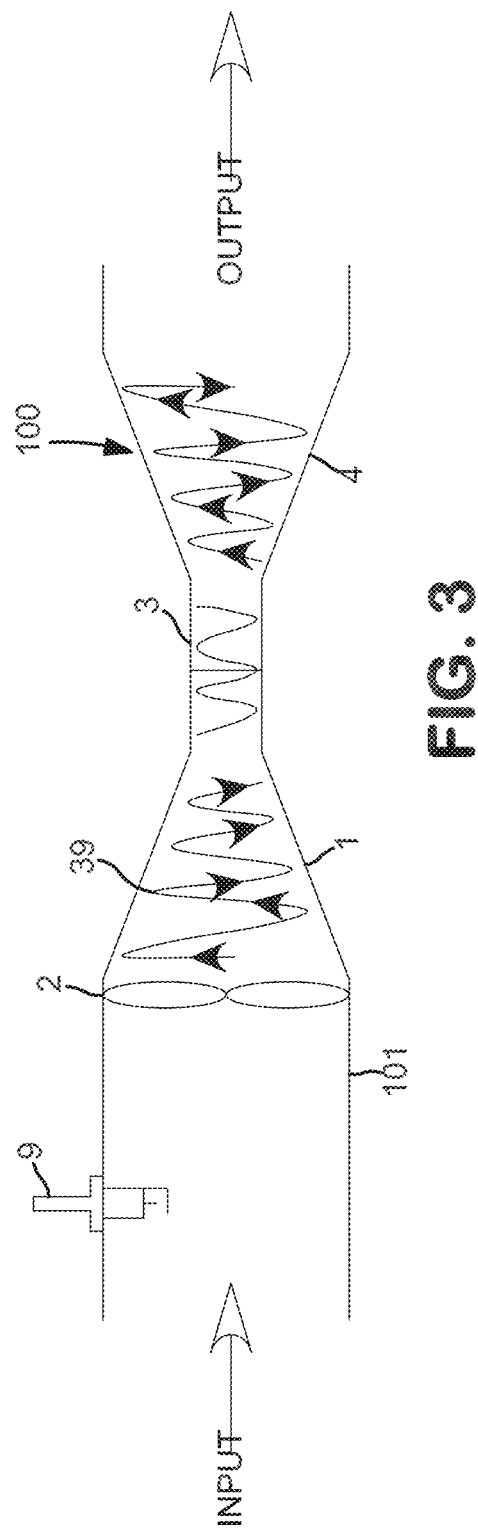

Example of liquid: $4\ CH_3OH + O_2 \rightarrow CO + 3H_2 + C_2H_2 + 2H_2O$

Example of gas reaction: $4\ CH_4 + O_2 \rightarrow 2CO + 7H_2 + C_2H_2$

METHOD, APPARATUS, AND COMPUTER-READABLE MEDIA FOR VORTEX ARC REACTOR

This application is a divisional of U.S. patent application Ser. No. 15/791,702, filed Oct. 24, 2017, which claims priority to U.S. Provisional Patent Appln. No. 62/411,761, filed Oct. 24, 2016, the entire contents of all which are incorporated herein by reference. The patent or application file contains at least one drawing executed in color. Copies of this patent or patent application publication with color drawing(s) will be provided by the Office upon request and payment of the necessary fee.

BACKGROUND OF THE INVENTION

1. Field of the Invention

The present invention relates to vortex arc reactor apparatus and method for the conversion of any flammable product into synthesis gas, primarily aromatic liquids, and water using no external energy source or catalyst to produce the reaction.

2. Description of Related Art

In 1836 Edmund Davy first discovered the chemical compound acetylene while experimenting with potassium carbide. When potassium carbide was reacted with water, acetylene gas was produced and became the means of lantern lighting for miners and, in some places, gaslights for town lighting. In 1859 Marcel Morran first produced acetylene by electric arc, using carbon electrodes while passing hydrogen gas through the arc chamber.

The German company BASF provided the first commercial acetylene gas process in the 1920's, with the first plant being built in the 1940's. These and other processes require intense quenching of the temperature of the reacted gas to "freeze" the reaction at acetylene and reduce the amount of liquids produced. Idaho National Laboratory (INL) patented the use of a converging/diverging nozzle in U.S. Pat. No. 7,097,675. This work followed the mathematical modeling of Chang and Pfender (Yl Change and E. Pfender, Plasma Chemistry and Plasma Processing, vol. 7, No. 3, p 275 (1987)), who predicted the temperature drop, or quenching effect of the converging/diverging nozzle. INL used a plasma torch with the feed stream to provide ionized gas for the reaction to occur.

Other U.S. patents directed to the underlying technology include the following, each of which is incorporated herein by reference.
U.S. Pat. No. 5,427,747 "Methods and Apparatus for Producing Oxygenates from Hydrocarbons"
U.S. Pat. No. 7,008,970 "Method for converting gaseous hydrocarbons to liquids"
U.S. Pat. No. 5,749,937 "Plasma fast quench reactor and method"
U.S. Pat. No. 5,935,293 "Continuation in part to U.S. Pat. No. 5/749,937"
RE37,853 "Fast quench reactor and method"
U.S. Pat. No. 6,187,226 "Hydrogen and elemental carbon production from natural gas and other hydrocarbons"
U.S. Pat. No. 7,097,675 "Fast quench reactor for hydrogen and elemental carbon production from natural gas and other hydrocarbons"
U.S. Pat. No. 3,395,194 "Process for preparing acetylene in an electric arc reactor"

However, all of the known apparatus and method require using at least one external energy source or catalyst to produce the reaction.

Thus, what is needed is apparatus and method for converting any flammable product into synthesis gas (e.g., aromatic liquids and water) using substantially no external energy source or catalyst to produce the reaction.

SUMMARY OF THE INVENTION

Thus, in view of the above, what is needed is a converging/diverging nozzle with an igniter to combust or at least partially combust a mixture of reactant and oxidant to produce a flame. The reaction output is provided to a gas-liquid separator which outputs the synthesis gas and liquid.

It is an advantage of the present invention to overcome the problems of the related art, and to provide a means to convert stranded natural gas, for example, into (i) synthesis gas for gas to liquids processes, and (ii) liquid hydrocarbons, without losing large portions of the gas for process heat rather than product. Heavy hydrocarbons and alcohols can thus be converted to synthesis gas and lighter hydrocarbon liquids without consuming natural gas or other fuels for process heat.

According to a first aspect of the present invention, apparatus for producing a syngas and at least one aromatic liquid has a nozzle with a converging portion, a throat portion, and a diverging portion. Input structure is configured to input a reactant and an oxidant into the converging portion of the nozzle. Ignition structure is configured to ignite the input reactant and oxidant. A vortex-creating structure is configured to create a vortex of the ignited reactant and the oxidant in the converging portion of the nozzle. The input structure, the vortex-creating structure, and the nozzle converging and throat portions are configured to provide a throat-portion-vortex of ignited reactant and oxidant that has an angular velocity which provides (i) negatively-charged particles in an exterior portion of the throat-portion-vortex, (ii) positively-charged particles in an interior portion of the throat-portion-vortex, and (iii) at least one reaction between the positively-charged particles and the negatively-charged particles, to form syngas and the at least one aromatic liquid in the nozzle diverging portion. Gas/liquid separation structure is configured to separate the formed syngas from the at least one aromatic liquid. A syn gas output outputs the syngas, and an aromatic liquid output outputs the aromatic liquid(s).

According to a second aspect of the present invention, a method for producing a syngas and at least one aromatic liquid disposes a nozzle having a converging portion, a throat portion, and a diverging portion. A reactant and an oxidant are input into the converging portion of the nozzle. The input reactant and oxidant are ignited. A vortex of the ignited reactant and the oxidant is created in the converging portion of the nozzle. The input structure, the vortex-creating structure, and the nozzle converging and throat portions are disposed so as to provide a throat-portion-vortex of ignited reactant and oxidant that has an angular velocity which provides (i) negatively-charged particles in an exterior portion of the throat-portion-vortex, (ii) positively-charged particles in an interior portion of the throat-portion-vortex, and (iii) at least one reaction between the positively-charged particles and the negatively-charged particles, to form syngas and the at least one aromatic liquid in the nozzle diverging portion. The formed syngas is then separated from the at least one aromatic liquid. The syn gas and the at least one aromatic liquid are preferably output separately.

BRIEF DESCRIPTION OF THE DRAWINGS

Exemplary embodiments of the presently preferred features of the present invention will now be described with reference to the accompanying drawings.

FIGS. 2a, 2b1, 2b2, and 2c are close-up views of the nozzle according to the FIG. 1 embodiment; showing configurations for forced draft and induced draft operations with different mechanisms to cause the rotation of flame into the converging section of the nozzle.

FIG. 3 is a diagram of the vortex produced in accordance with the FIG. 1 embodiment.

DETAILED DESCRIPTION OF THE PRESENTLY PREFERRED EXEMPLARY EMBODIMENTS

Briefly, the present invention is directed to a system and method for the conversion of combustible or at least partially combustible compounds into synthesis gas and liquid hydrocarbons. Long chain hydrocarbons and alcohols, such as fuel oil, can be converted into shorter chain hydrocarbons and synthesis gas. Natural gas, especially in small quantity situations such as from an oil well, can be converted and processed with this embodiment to reduce or eliminate the need for flaring such stranded gas. Systems currently on the market can use as much as 99% of the gas as fuel to make steam for a steam methane reformer so that the 1% can be converted via gas-to-liquids technologies.

Figure 1:
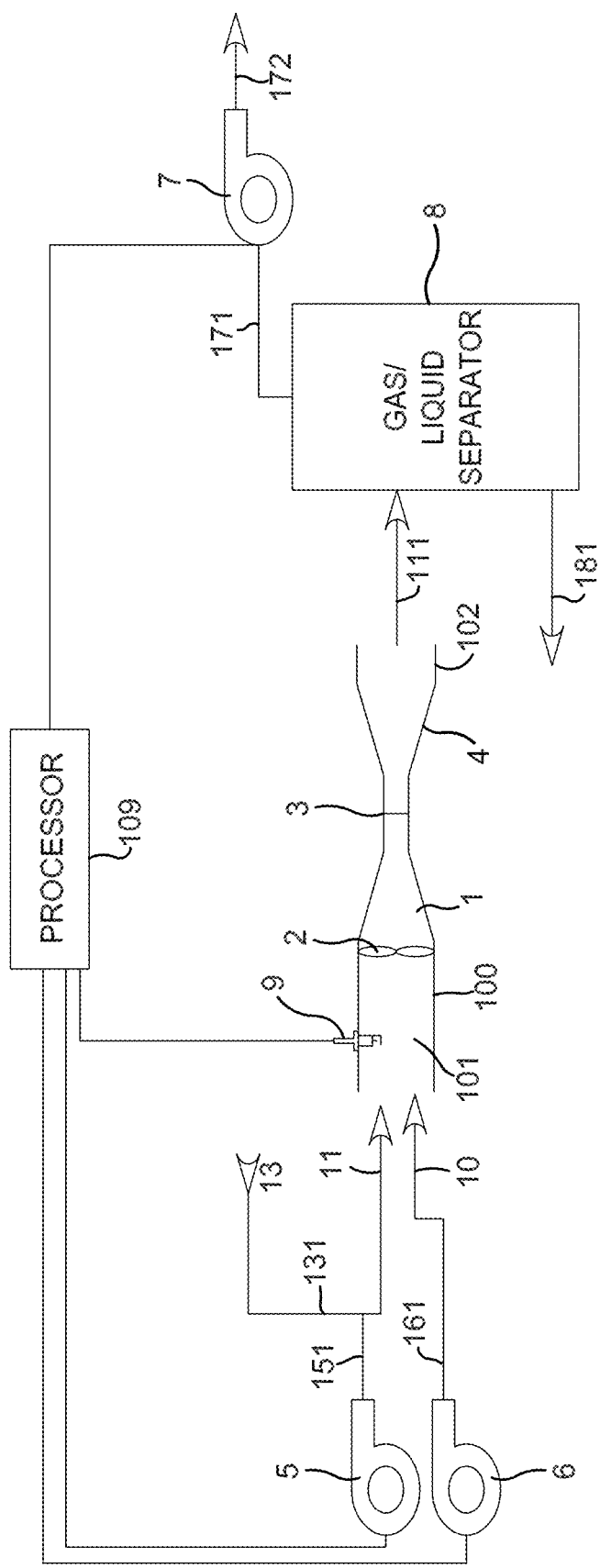
FIG. 1 is a block diagram of an embodiment according to the present invention.

The FIG. 1 embodiment preferably utilizes the work J. Wu, J. Sheridan, K. Hourigan, J. Soria from there article "Shear layer vortices and longitudinal vortices in the near wake of a circular cylinder" published in Experimental Thermal and Fluid Science 12(2):169-174 February 1996 (the entire contents of which are incorporated herein by reference), showing that when Reynolds Numbers are above 3000, at least two shear layers develop in vortices. The Reynolds number is, in part, calculated by the velocity of the fluid and the "roughness" of the cylinder wall. In fluid mechanics, the Reynolds number (Re) is a dimensionless quantity that is used to help predict similar flow patterns in different fluid flow situations. The Reynolds number is defined as the ratio of inertial forces to viscous forces and consequently quantifies the relative importance of these two types of forces for given flow conditions. Reynolds numbers frequently arise when performing scaling of fluid dynamics problems, and as such can be used to determine dynamic similitude between two different cases of fluid flow. They are also used to characterize different flow regimes within a similar fluid, such as laminar or turbulent flow. The Reynolds number is defined as:

$$\text{Reynolds Number} = \frac{\text{Inertial Force}}{\text{Viscous Force}} \quad (1)$$

$$Re = \frac{\rho V L}{\mu} \quad (2)$$

Where,
$\rho$ is the density of the fluid,
V is the velocity of the fluid,
$\mu$ is the viscosity of fluid, and
L is the length or diameter of the fluid.

This is important in the consideration of the charged particles in a flame. A flame is an ionized gas, whether a plasma or not, and carries free charges, both positive and negative. See article "The distribution of excess charges in the diffusion flame of hydrocarbons" S M Reshetnikov, I A Zyryanov, A P Pozolotin and A G Budin Physics Department, Vyatka State University, 610000, Kirov, Moskowskaya Street, 36, Russia (the entire contents of which are incorporated herein by reference). From this article it is noted that when a flame is lacking in an oxidant, or partial combustion is occurring, then the base of the flame has a negative potential. This is explained by negatively charged carbon (or soot particles) in the flame.

In the present embodiment, these negatively charged carbon (or soot) particles are moved to the outside of the vortex by centrifugal force in the nozzle. As this occurs in the converging section, the carbon (or soot) forms an electrode in the outer shear layer.

Positive charged hydrogen ions, being much lighter than carbon, will at least partially stay in the middle shear layer of the vortex's lower angular momentum. Positive ions are produced in flame as seen in the commonly used gas chromatography-flame ionization detector used in labs around the world where the ionization levels are used to identify the gases being tested. Also, from "Ionic structures of methane flames" Timothy Wayne Pederson, Iowa State University 1991, page 17 (the entire contents of which are incorporated herein by reference), see a table of ionic species in flames.

In FIG. 1, a nozzle 100 comprises an input section 101, a converging section 1, a nozzle throat 2, a diverging section 4, and an output section 102. Preferably, the input section is about 3-9 inches long, more preferably about 4-8 inches long, even more preferably about 5-7 inches long, and most preferably about 6 inches long. The input section is preferably about 0.5-4 inches in diameter, more preferably about 1-3.5 inches in diameter, even more preferably about 1.5-3 inches in diameter, and most preferably about 2 inches in diameter. Note that all dimensions given herein are for the current embodiment, and it is envisaged that the process and apparatus may be scaled to any reasonable size, including but not limited to one, two, three, four, five or more orders of magnitude (×10) larger than those stated herein.

Preferably, the converging section is about 1-5 inches long, more preferably about 2-4 inches long, even more preferably about 3 inches long. Preferably, the converging section has a diameter at an opening portion that matches the diameter of the input section, and narrows to the diameter of the throat section, to be described below.

Preferably, the throat section is about 0.5-4 inches long, more preferably about 1-3.5 inches long, even more preferably about 1.5-3 inches long, and most preferably about 2 inches long. Preferably, the throat section is about 0.25-2 inches in diameter, more preferably about 0.5-1.5 inches in diameter, and most preferably about ¾ inches in diameter.

Preferably, the diverging section mirrors the converging section, with similar dimensions to those give above. Likewise, the output section preferably mirrors the input section, again with similar dimensions to those stated above.

An igniter 9 is preferably provided in the input section 101, but may comprise a plurality of nozzles provided in and/or about the input section 101 and/or the converging section 1.

Preferably, the igniter (e.g., one or more spark plugs) is controlled by one or more processor 109 (FIG. 1) under control of code stored in one or more computer-readable media. Preferably, the processor(s) 109 also control the blowers to be described below, and thus the flow and pressure of the reactant and the oxidant through the nozzle.

The one or more processors 109 may be embodied in one or more Personal Computers (PCs), one or more (cloud-based) servers, one or more personal computing devices, one or more field programmable gate array (FPGA) one or more application-specific integrated circuit (ASIC), or one or more digital signal processor (DSP), or any combination of these.

The words computational device, computer and device are used interchangeably and can be construed to mean the same thing.

A "device" in this specification may include, but is not limited to, one or more of, or any combination of processing device(s) such as, a cell phone, a Personal Digital Assistant, a smart watch or other body-borne device (e.g., glasses, pendants, rings, etc.), a personal computer, a laptop, a pad, a cloud-access device, a white board, and/or any device capable of sending/receiving messages to/from a local area network or a wide area network (e.g., the Internet), such as devices embedded in cars, trucks, aircraft, household appliances (refrigerators, stoves, thermostats, lights, electrical control circuits, the Internet of Things, etc.).

As used herein, a "server", a "computer", a "device", and all of the processor-based structure noted above may comprise one or more processors, one or more Random Access Memories (RAM), one or more Read Only Memories (ROM), one or more user interfaces, such as display(s), keyboard(s), mouse/mice, etc.

The servers and devices in this specification typically use the one or more processors to run one or more stored "computer programs" and/or non-transitory "computer-readable media" to cause the device and/or server(s) to perform the functions recited herein. The media may include Compact Discs, DVDs, ROM, RAM, solid-state memory, or any other storage device capable of storing the one or more computer programs.

Returning to FIG. 1, one or more reaction input pipe/tube 11 supplies the hydrocarbon input, as will be described in greater detail below. The hydrocarbon may come from a reaction supply system 13 through one or more pipe/tube 131 and/or from one or more reactant blower/compressor 5 through one or more pipe/tube 151. One or more air and/or oxygen pipe/tube 161 supplies the oxidizer, preferably from one of more forced draft blower 6.

The blower(s) 5,6 provide the reactant and oxidizer to the input 101 (at about 10 inches of H2O pressure and preferably more than 16 cubic feet per minute combined) where they are ignited by ignitor(s) 9. A preferable reactant is at least 2 cubic feet per minute for propane, and a preferable oxidant is at least 14 cubic feet per minute of ambient air when the reactant is propane.

A preferably fixed mechanism is installed in the input section 101 (or inside the converging section 1) and swirls the burning reactant/oxidizer into a vortex. A preferred fixed mechanism is a fixed fan blade 2, of FIG. 2b2, such that the angle of the blade 24 is less than 45 degrees from perpendicular outer ring 22 to the length of the input section 100. An alternative embodiment comprises a conical helix 29 (FIG. 2c) designed such that flow will preferably be rotated by the grooves 292, 293 in the converging section 1. This vortex is then compressed in the converging section 1 and the nozzle throat 3, making the vortex smaller and increasing its speed. After exiting the nozzle throat 3, the swirling vortex passes through the diverging section 4 and the output section 102. The vortex operations and layers will be described in greater detail below.

Figures 4, 5:
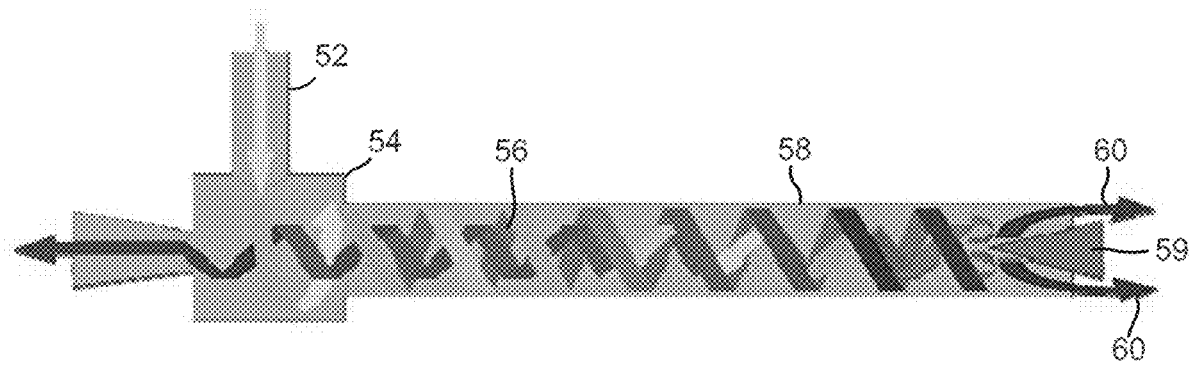
FIG. 4 is a diagram of the chemical reaction produced in accordance with the FIG. 1 embodiment.
FIG. 5 is a schematic block diagram of the vortex flow within a vortex heater/cooler, showing how layers can form in a vortex, according to the prior art.
Figure 6A:
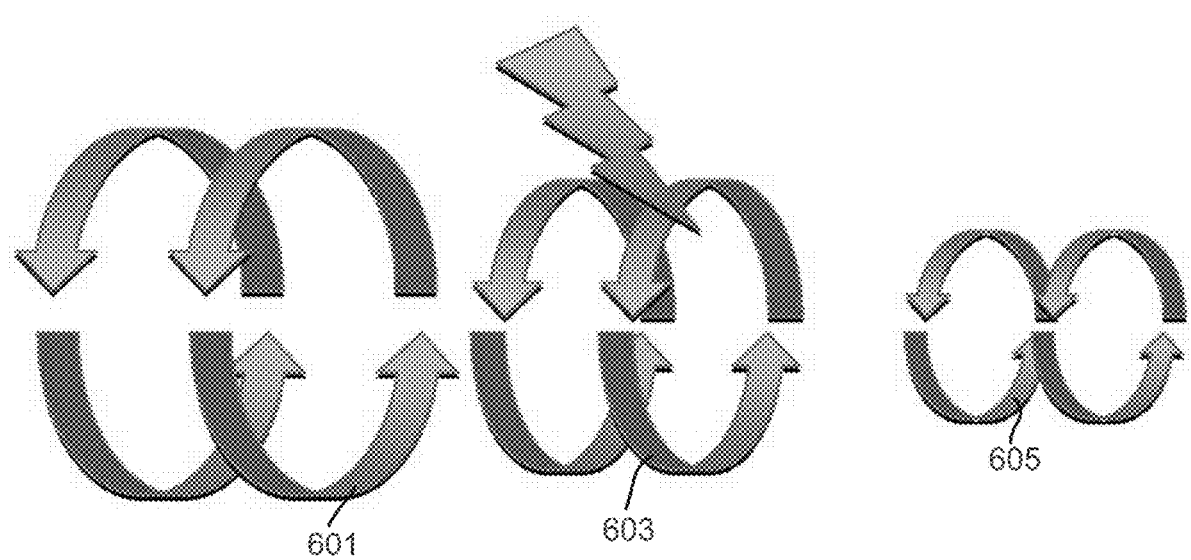
FIGS. 6a, 6b, 6c, and 6d are schematic views of a vortex produced in accordance with the principles of the present invention, showing the various formed layers.

As shown schematically in FIG. 6a, plural layers form in the vortex, setting up at least an outer layer 601, a separation layer 603, and an inner layer 605. The rotation in FIG. 6a is counter clockwise when viewed along a longitudinal axis of the vortex, from the inner layer end. The outer layer 601 typically has the highest velocity of about 9.5 m/sec (meters/second) or higher, and highest pressure of about 1.18 Pa (Pascal) at that velocity, while the separation layer 603 has a somewhat lower velocity, about 7 m/sec, and lower pressure of about 0.91 Pa at that velocity. The inner layer 605 preferably has the lowest velocity at about 1 m/sec and the lowest pressure of about 0.1 Pa at that velocity. This layer separation, along with the charge separation (positively charged particles toward the inner layer, and negatively charged particles toward the outer layer) allows for electrical discharge between the layers; this is called arcing and sparking. The arcing and sparking releases much energy, leading to a quicker and easier chemical reaction as shown in FIG. 4.

Figure 6B:
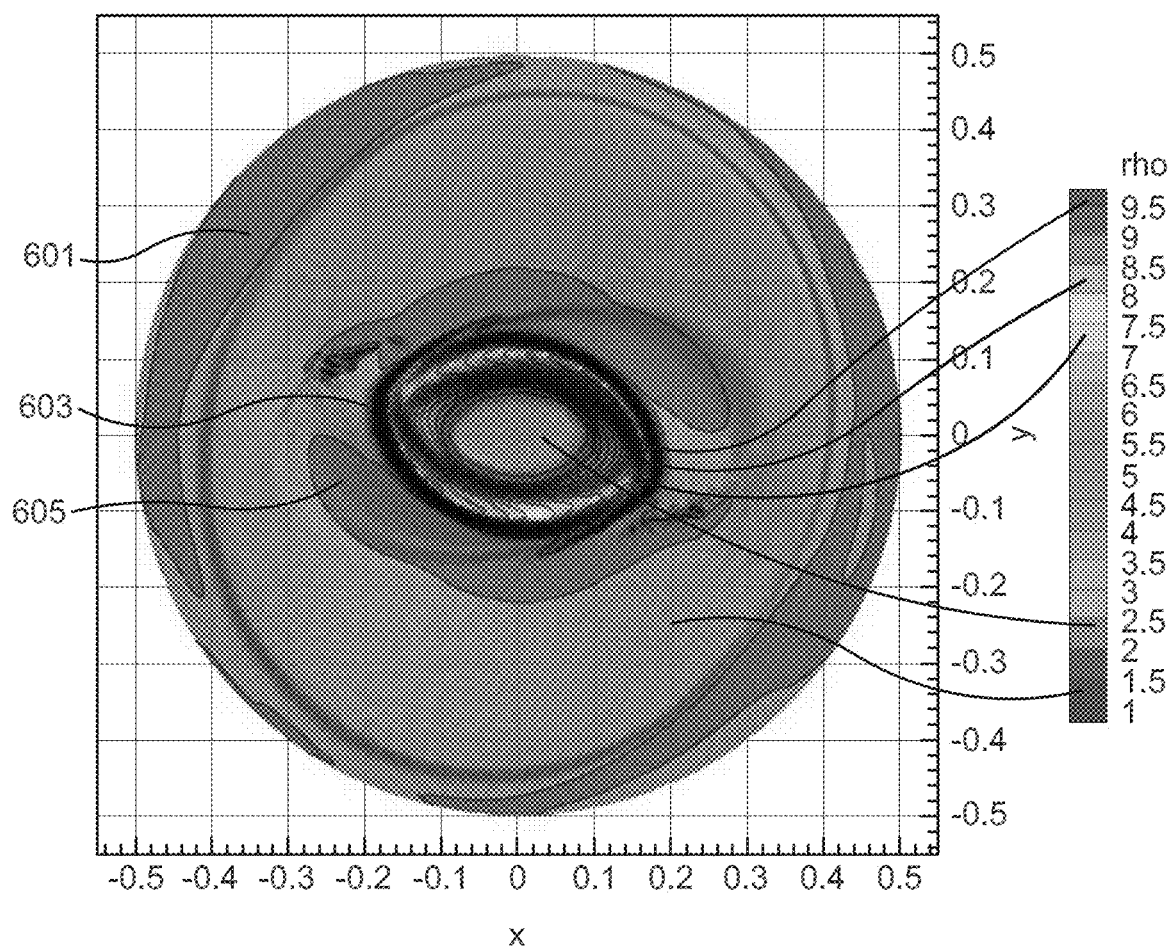

FIG. 6b shows the vortex from the axial end view, depicting separation of layers by velocity. As can be seen, the highest velocities (about 9.5 m/sec to about 4.0 m/sec) appear in the separation layer 603, while lower velocities (about 1.0 m/sec to about 3.5 m/sec) appear in the outer layer 601 and the inner layer 605.

Figure 6C:
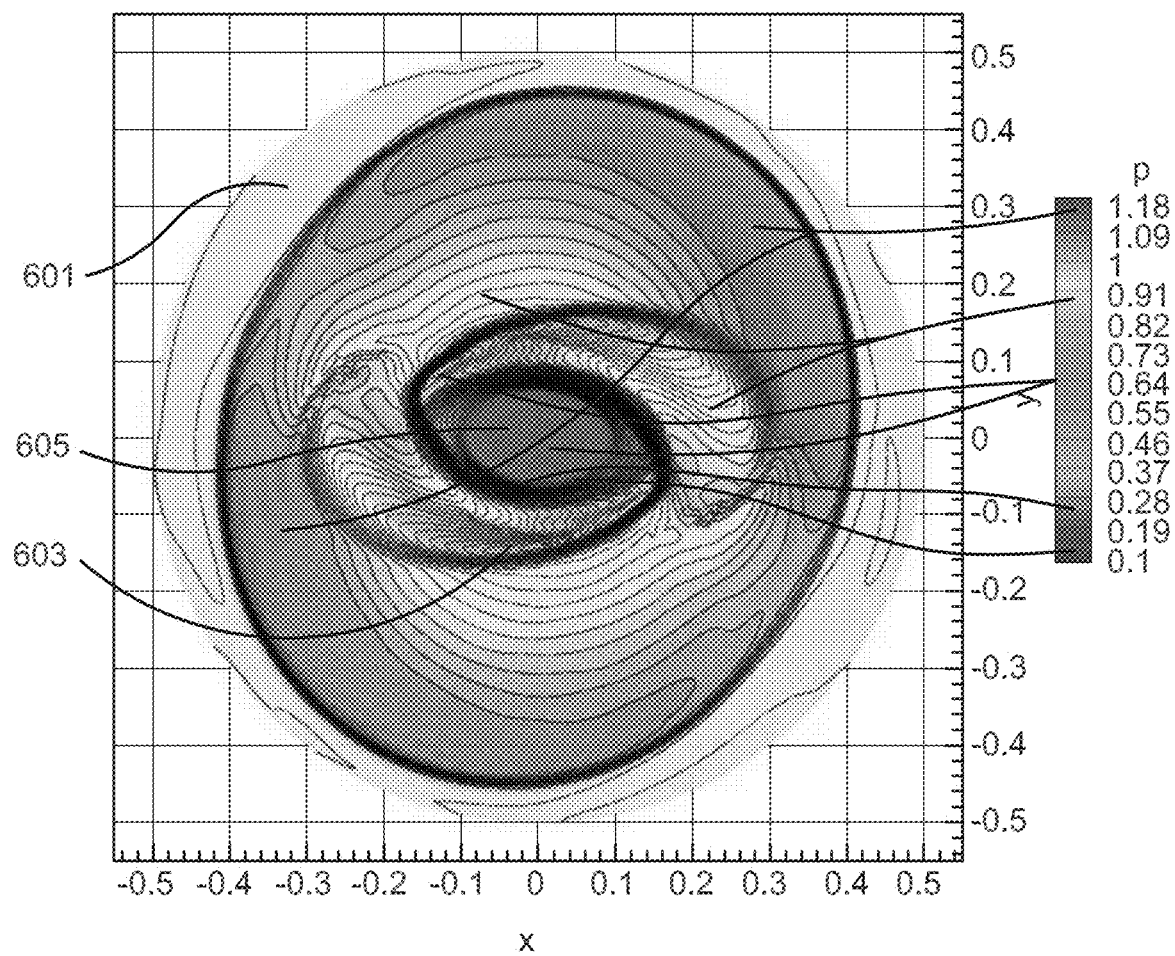

FIG. 6c shows the vortex from the axial end view, depicting separation of layers by pressure. The highest pressures (from about 1.18 Pa to about 0.82 Pa appear in the outer layer 601, and somewhat in the separation layer 603. Mid-range pressures (from about 0.91 to about 0.37) appear in the separation layer 603. And the lowest pressures (from about 0.37 to about 0.1) appear in the inner layer 605.

Figure 6D:
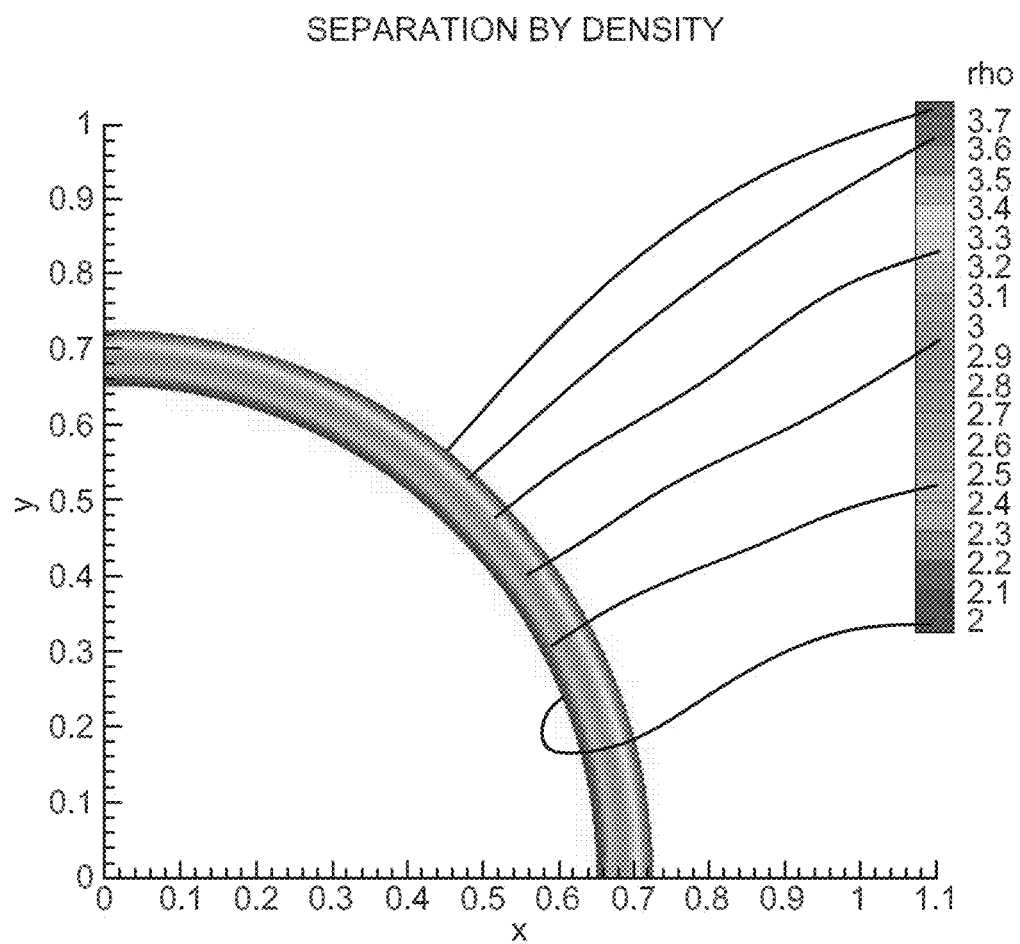

FIG. 6d shows the vortex from the axial end view, depicting separation of layers by density. As can be seen, the outer layer in this example has a density ($\rho$) rho of 3.7 kg/m3 with an inner density of 2 ($\rho$) kg/m$^3$.

The vortex illustrations in FIGS. 6a, 6b, 6c, and 6d are easily understandable from the point of view of magneto-hydrodynamic (MHD) formulations (the study of magnetic properties of electrically conducting fluids), which hold to the fundamental concept behind MHD that magnetic fields can induce currents in a moving conductive fluid, which in turn polarizes the fluid and reciprocally changes the magnetic field itself. This induces electric arcing and sparking, as described in "Simulation of Electric Arc Extinction in a Simple Electric Network", P. Delmont & M. Torrilhon, MathCCES, Department of Mathematics, RWTH Aachen, Germany, December 2012 (the entire contents of which are incorporated herein by reference). Arcing happens when an electric potential is applied across a highly resistive gaseous medium such as carbon monoxide that ideally should be in a layer with hydrogen and opposite the carbon or soot. This layering thus produces a potential difference causing the current to jump between the layers (arc).

After leaving the output section 102 the reaction products are supplied to a gas/liquid separator 8 through one or more output pipe/tube 111. Preferably, one or more blower/compressor 7, coupled to a top of the gas/liquid separator 8 via one or more pipe/tube 17, pulls at least a partial vacuum (e.g., 13-14 psi absolute) at the top of the gas/liquid separator 8, and provides the syngas output through one or more output pipe/hose 172. The liquid from the gas/liquid separator 8 is preferably output from a bottom of the gas/liquid separator via one or more pipe/tube 181.

The angular velocity of the vortex is calculated by Leonhard Euler's turbine formula:

$$e^{ix} = \cos x + \sin x \quad (3)$$

where e is the base of the natural logarithm, i is the imaginary unit, and cos and sin are the trigonometric functions cosine and sine respectively, with the argument x given in radians. With angular velocities as low as 50 M/s to over 3000 M/s, with higher velocities in the outer section and slower velocities in the inner, the charges will stabilize between the positive and negative, in part due to centrifugal forces moving the charged particles. This sets up the potential difference to allow electrical discharges between the at least two species of charged particles.

French physicist Georges Ranque first invented a device known as a Ranque-Hilsch vortex tube in 1931. German physicist Rudolf Hilsch improved on the device and published a paper in 1947 called Wirbelrohr (whirling pipe). The device was widely used to separate gas mixtures such as oxygen and nitrogen by Linderstrom-Lang starting in 1967 which demonstrates the centrifugal action of the vortex. See FIG. 5. In FIG. 5, air is introduced at 52 where a swirling vortex pattern 56 is induced by injecting air along the side in the larger cylinder section 54. The pressure of the input air can be 100 PSIG or higher. A nozzle obstruction 59 causes an outflow of hot oxygen rich air at 60. Cold low-oxygen air is output from nozzle 61.

The Wiedemann Franz Law is a comparison of electrical conductivity to thermal conductivity. The Wiedemann-Franz law is the ratio of the electronic contribution of the thermal conductivity ($\kappa$) to the electrical conductivity ($\sigma$) of a metal, and is proportional to the temperature (T), where L is the Lorenz number.

$$\kappa/\sigma = LT \quad (4)$$

This law is generally applied to metal, but is known to be accurate in materials with free electron movement. In ionized gas (flame) electrons are free to move, thus making the law applicable in this instance. See MECHANISM OF ION FORMATION IN HIGH-TEMPERATURE FLAMES By TAKAYUKI FUENO, NALIN R. MUKHERJEE, TAIKYUE REE AND HENRY EYRING, Symposium (International) on Combustion, Volume 8, Issue 1, 1961, pages 222-230 (the entire contents of which are incorporated herein by reference). This makes the separation of temperatures in the Ranque-Hilsch vortex tube applicable to the separation of charges described in this embodiment.

In operation, in FIG. 1, a reactant (such as, but not limited to, natural gas) is mixed with air or oxygen at a pressure as low as 1" H20 up to about 40 pounds per square inch. The mixture is ignited by the ignitor(s) and flows to the stationary mechanism 2 to cause rotation. The rotating gas passes through the converging section 1 of the nozzle 100 to the throat 3. This throat length can vary based on the desired output from 0.032 inches up to about 3 feet; longer lengths should produce longer chain liquid aromatics.

The swirling gases then pass through the diverging section 4 of the nozzle where the rapid expansion causes the quenching effect. The angular and linear acceleration of the gases through the converging section 1 causes a drop in temperature, as described by Chang and in the Idaho National Laboratory work described herein, as the fast quench phenomenon is achieved by rapidly converting thermal energy in the plasma gas to kinetic energy via a modified adiabatic and isentropic expansion through a converging-diverging nozzle. The rapid expansion of the gas through the diverging section 4 then stops the reaction as the thermal energy has now been converted from thermal energy to kinetic energy into chemical potential energy in the products such as hydrogen. This quenching effect is the reason for the varying length possibility of the nozzle throat 3 as the thermal to chemical conversion stops with the adiabatic and isentropic expansion of the diverging section 4. See FIG. 4 for the chemical reaction that takes place.

From the diverging section 4 of the nozzle, the gas passes into a cylinder 8, either vertical or horizontal, to separate the liquids from gases. With a vertical cylinder, it would be filled preferably with commercial tower packing to produce surface area for compounds to condense onto and build in size until the drops are pulled down by gravity where they would be pumped out. In a horizontal system all mass is passed into one end of the cylinder by the motive force of the system. Hydrocarbon liquids rise above water due to specific gravity allowing the gas portion of the mass to push the oil to a weir overflow and the gas to then rise vertically into piping for use as either gas to liquids feedstock or into a combustion process.

FIG. 2a is a side view of an embodiment according to the present invention where the swirling fluid flow is produced by forced draft. In this embodiment, one or more of the blower(s) 5,6 provide a forced flow of the mixed reactant(s)/oxider(s) into the nozzle 100. The fixed mechanism 2 causes the mixing/mixed gases (fluids) to begin swirling in the vortex pattern, at a given speed. As the nozzle converges, the vortex of gasses/fluids picks up angular speed, causing the separation of the positively-charged and negatively-charged particles, as described above. The fixed mechanism 2 is further depicted in FIGS. 2b1 and 2b2. Preferably, the mechanism 2 comprises a disc-shaped plate 22 made of metal, plastic, composites, or any other material capable of withstanding the volumes and heats generated by the nozzle apparatus. The plate 22 has one or more openings 23, and one or more bent flanges 24, which are bent at an angle (e.g., between 3 and 70 degrees) sufficient to force the swirling vortex pattern of gasses/fluids.

FIG. 2c is a side view of an embodiment according to the present invention where the vortex fluid flow is produced by induction. In FIG. 2c, the one or more of the blower(s) 5,6 provide a flow of the mixed reactant(s)/oxidizer(s) into the nozzle 100. The fixed mechanism 29 causes the mixing/mixed gases (fluids) to begin swirling in the vortex pattern, at a given speed. Preferably, the mechanism 29 has a conical and/or frusto-conical shape with numerous helical grooves 293 reducing in diameter from a broad end 291 to a narrower end 292 thereof. Preferably, the mechanism 29 is disposed within the converging section 1 from an opening end thereof to the portion which assumes a fixed diameter adjacent or in the throat 3. By forcing the gasses/fluids to flow in a helical/swirling/vortex pattern in the converging portion 1, the proper vortex pattern is induced in the throat 3, where the oppositely-charged particles are disposed.

FIG. 3 is a side-view diagram of the vortex produced in accordance with the FIG. 1 embodiment. As can be seen, the fixed mechanism sets up the vortex pattern 39 at the outlet to the input section 101, adjacent the inlet to the converging section 1. The swirling/vortex pattern moves in the clockwise direction (although it could just as easily be in the counter-clockwise direction). As the vortex of gasses/fluids is compressed and speeded-up in the converging section 1, the negatively-charged particles begin to migrate toward the outer portion of the vortex, while the positively-charged particles begin to migrate toward the central portion of the vortex. In the throat portion 3, the vortex assumes a substantially constant diameter, and the charged particles become aligned with the inner and outer portion of the vortex. This is where the most substantial portion of the chemical reaction depicted in FIG. 4 takes place.

With respect to FIG. 4, chemical reactions such as the one represented by this equation would occur in this embodiment. 4 $CH3OH+O2->CO+3H2+C2H2+2H2O$. Where methanol is combusted at a lower flammability limit producing carbon monoxide, hydrogen, acetylene, and water. Commercial acetylene processes rely on fast quench methods to "freeze" this reaction at acetylene. However, if quenching is delayed, acetylene molecules will react with each other to produce longer chain aromatics.

Another example would be methane; 4 $CH4+O2->2CO+7H2+C2H2$. Here again, methane is combusted at a lower flammability limit to produce carbon monoxide, hydrogen, and acetylene. Efficiency is a factor in the output of any reaction through this and any embodiment, but these examples show how the output is affected by the input. In both examples here, these reactions can only occur at temperature not possible by combustion but only by the thermal equivalent of an electric arc, which is 35,000 degrees Fahrenheit. The production of hydrogen gas has to be at least at its dissociation temperature of 5500 degrees Fahrenheit.

The individual components shown in outline or designated by blocks in the attached Drawings are all well-known in the synthesis gas arts, and their specific construction and operation are not critical to the operation or best mode for carrying out the invention.

While the present invention has been described with respect to what is presently considered to be the preferred embodiments, it is to be understood that the invention is not limited to the disclosed embodiments. To the contrary, the invention is intended to cover various modifications and equivalent arrangements included within the spirit and scope of the appended claims. The scope of the following claims is to be accorded the broadest interpretation so as to encompass all such modifications and equivalent structures and functions.

What is claimed is:

1. A method for producing a syngas and at least one aromatic liquid, comprising:
    disposing a nozzle having a converging portion, a throat portion, and a diverging portion;
    inputting a reactant and an oxidant into an input section upstream at the converging portion of the nozzle;
    igniting the input reactant and oxidant in the input section to combust or partially combust a mixture of the reactant and the oxidant;
    supplying the combusted or partially combusted mixture to a gas flow rotator disposed in the input section or the converging portion to create a vortex of the combusted or partially combusted mixture in the converging portion of the nozzle, wherein the gas flow rotator comprises a disc-shaped plate that is spatially fixed and comprises one or more openings and one or more flanges that are bent at an angle from a disc-shaped surface of the disc-shaped plate to create the vortex of the combusted or partially combusted mixture, and wherein the disc-shaped surface is oriented to face a flow of the supplied combusted or partially combusted mixture; and
    supplying the vortex of the combusted or partially combusted mixture to the throat portion of the nozzle which is configured to induce (i) negatively-charged particles in an exterior portion of the vortex in the throat portion, (ii) positively-charged particles in an interior portion of the vortex in the throat portion, and (iii) at least one reaction between the positively-charged particles and the negatively-charged particles, to form the syngas and the at least one aromatic liquid in the nozzle diverging portion.

2. The method according to claim 1, further comprising outputting the formed syngas and the at least one aromatic liquid through an output structure downstream from the diverging portion of the nozzle.

3. The method according to claim 1, further comprising:
    separating the formed syngas from the at least one aromatic liquid;
    outputting the syngas; and
    outputting the at least one aromatic liquid.

4. The method according to claim 1, wherein the at least one reaction between the positively-charged particles and the negatively-charged particles in the throat portion includes arcing.

5. The method according to claim 1, wherein the gas flow rotator and the converging and throat portions are configured so as to increase an angular velocity of the combusted or partially combusted mixture in the vortex in the throat portion.

6. The method according to claim 1, wherein the gas flow rotator and the converging and throat portions are configured so as to form, in the vortex in throat portion, at least (i) an outer layer, (ii) a separation layer, and (iii) an inner layer.

7. The method according to claim 1, further comprising controlling the inputting of the reactant and the oxidant using at least one processor.

8. The method according to claim 1, wherein the flanges of the disc-shaped plate comprises a multi-bladed structure.

9. At least one non-transitory computer readable storage medium which stores one or more computer programs, the one or more programs comprising instructions, which when executed by one or more processors perform a method for producing a syngas and at least one aromatic liquid using a structure comprising: (i) a nozzle having a converging portion, a throat portion, and a diverging portion; (ii) an input section upstream at the converging portion wherein a reactant and an oxidant are input into the input section; (iii) an igniter disposed in the input section for igniting the input reactant and oxidant; (iv) a gas flow rotator disposed in the input section or the converging portion;
    the method comprising:
        controlling the input section and the igniter so as to:
            ignite the input reactant and oxidant in the input section to combust or partially combust a mixture of the reactant and the oxidant;
            supply the combusted or partially combusted mixture to the gas flow rotator to create a vortex of the combusted or partially combusted mixture in the converging portion of the nozzle, wherein the gas flow rotator comprises a disc-shaped plate that is spatially fixed in the input section or the converging portion and comprises one or more openings and one or more flanges that are bent at an angle from a disc-shaped surface of the disc-shaped plate to create the vortex of the combusted or partially combusted mixture, and wherein the disc-shaped surface is oriented to face a flow of the supplied combusted or partially combusted mixture; and supply the vortex of the combusted or partially combusted mixture to the throat portion of the nozzle which is configured to induce (i) negatively-charged particles in an exterior portion of the throat-portion-vortex, (ii) positively-charged particles in an interior portion of the throat-portion-vortex, and (iii) at least one reaction between the positively-charged particles and the negatively-charged particles, to form the syngas and the at least one aromatic liquid in the nozzle diverging portion.

10. The non-transitory computer readable storage medium according to claim 9, wherein the flanges of the disc-shaped plate comprises a multi-bladed structure.

* * * * *